United States Patent [19]

Beranger et al.

[11] 4,181,722

[45] Jan. 1, 1980

[54] CHROMENE DERIVATIVES USEFUL AS BRONCHODILATORS AND ANTI-ARRHYTHMICS

[75] Inventors: Serge Beranger, Bretigny-sur-Orge; Henri Pinhas, Paris, both of France

[73] Assignee: Laroche Navarron S.A., Puteaux, France

[21] Appl. No.: 901,834

[22] Filed: May 1, 1978

[30] Foreign Application Priority Data

May 9, 1977 [GB] United Kingdom ............... 19351/77

[51] Int. Cl.² .................... A61K 31/495; A61K 31/35; C07D 311/58; C07D 405/06
[52] U.S. Cl. ............................... 424/250; 260/345.2; 544/364; 544/376; 546/196; 546/269; 424/263; 424/267; 424/283
[58] Field of Search ................ 544/376, 364; 546/196, 546/269; 260/345.2; 424/250, 263, 267, 283

[56] References Cited

U.S. PATENT DOCUMENTS 3,374,245  3/1968  Carney et al. ..................... 544/376
3,959,281  5/1976  Beyerle et al. ..................... 544/376

Primary Examiner—Paul M. Coughlan, Jr.

Attorney, Agent, or Firm—Young & Thompson

[57] ABSTRACT

The present invention relates to compounds of the general formula:

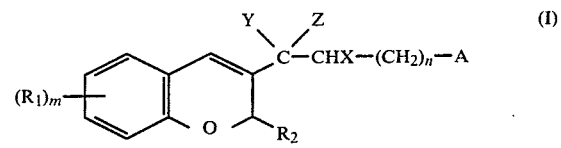

in which:
$R_1$ is selected from hydrogen and alkoxy having 1–7 carbon atoms,
$R_2$ is hydrogen,
n is selected from zero and 1,
X and Y are hydrogen atoms, and
Z is hydroxy, or
Y and Z taken together represent an oxygen atom, or, when n=1, X and Z may represent a single bond,
A represents an amino radical, and their pharmaceutically acceptable acid addition salts.

These compounds are useful in particular for the treatment of asthma.

8 Claims, No Drawings

CHROMENE DERIVATIVES USEFUL AS BRONCHODILATORS AND ANTI-ARRHYTHMICS

This invention relates to new chromene derivatives, to a process for their preparation and to their applications, typically for therapeutic purposes.

This invention relates to compounds having the general formula:

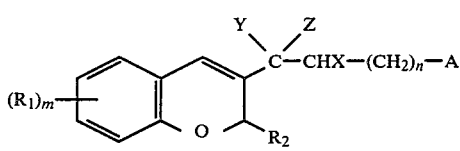

in which:

the radicals $R_1$ represent independently a hydrogen atom, a trifluoromethyl radical, a straight- or branched-chain alkyl radical having 1–12 carbon atoms, a cycloalkyl radical having 3–7 carbon atoms, an alkoxy radical having 1–7 carbon atoms, a cycloalkyloxy radical having 3–7 carbon atoms, an alkylene dioxy radical having 2–4 carbon atoms, a hydroxy radical or a halogen atom and m is 1 or 2, $R_2$ represents a hydrogen atom or an alkyl radical having 1–7 carbon atoms, particularly methyl, n is zero or 1, X and Y represent hydrogen atoms, and Z is a hydroxy radical, an alkoxy radical having 1–12 carbon atoms or an alkanoyloxy radical having 1–7 carbon atoms, or Y and Z represent together represent an oxygen atom, or when n=1, X and Z may also represent a single bond, A represents an amino radical selected from the morpholino radical, the radicals having the formula

in which $R_3$ and $R_4$ represent independently a hydrogen atom, an alkyl radical having 1–7 carbon atoms or a cycloalkyl radical having 3–7 carbon atoms, or $R_3$ and $R_4$, together with the nitrogen atom to which they are attached, form a piperidino radical optionally substituted with a phenyl group, or with a phenyl group and a cyano group, or a tetrahydropyridyl radical optionally substituted with a phenyl group, the radicals having the formula

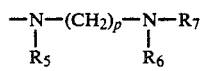

in which p is 2, 3 or 4, $R_5$ and $R_6$ represent independently a hydrogen atom, an alkyl radical having 1–7 carbon atoms or a cycloalkyl radical having 3–7 carbon atoms, and $R_7$ represents a hydrogen atom, an alkyl radical having 1–7 carbon atoms, a cycloalkyl radical having 3–7 carbon atoms, or an aryloxyalkyl radical having 1–7 carbon atoms in the alkyl moiety or an arylthioalkyl radical having 1–7 carbon atoms in the alkyl moiety, the radicals having the formula

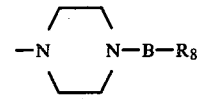

in which B represents a single bond or an alkylene radical having 1–10 carbon atoms, or a hydroxyalkylene radical having 2–3 carbon atoms optionally etherified with an alkyl radical having 1–7 carbon atoms or esterified with an alkylcarbonyl radical having 1–6 carbon atoms in the alkyl moiety such as for example the radicals

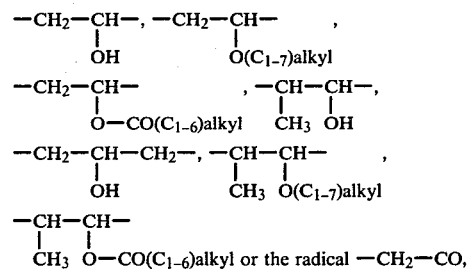

$CH_3$  $O-CO(C_{1-6})alkyl$  or the radical $-CH_2-CO$, $R_8$ represents a hydrogen atom, a phenyl, phenoxy, phenylthio, furyl, thienyl, pyridyl or chromenyl radical, said radicals being optionally mono-, di- or tri-substituted with a hydrogen atom, a trifluoromethyl radical, a hydroxy radical, an alkyl radical having 1–7 carbon atoms, an alkoxy radical having 1–7 carbon atoms, a $CH_2OH$ radical, a halogen atom, an alkanoyloxy radical having 1–7 carbon atoms, a $COOalkyl$ radical having 1–7 carbon atoms in the alkyl moiety, a $CH_2Oalkyl$ radical having 1–7 carbon atoms in the alkyl moiety, a $CH_2OCOalkyl$ radical having 1–6 carbon atoms in the alkyl moiety, a $COO-COalkyl$ radical having 1–6 carbon atoms in the alkyl moiety, or an alkylenedioxy radical having 2–4 carbon atoms, and their pharmaceutically acceptable acid addition salts.

The addition salts may typically be those formed with hydrohalic acids, sulfuric acid, nitric acid, phosphoric acid, formic acid, acetic acid, maleic acid, fumaric acid, methane sulfonic acid, lactic acid, succinic acid, tartaric acid and acidic metal salts such as disodium orthophosphate and monopotassium sulfate.

In addition, the free bases may occur in the hydrated or the substantially anhydrous state.

A specific class of the compounds of the formula (I) is that consisting of the compounds of the formula (I) in which:

$R_1$ represents a hydrogen atom or an alkoxy radical having 1–7 carbon atoms, $R_2$ represents a hydrogen atom, m is 1, n is zero or 1, X and Y represent hydrogen atoms, and Z represents a hydroxy radical, or X and Z taken together represent an oxygen atom, or, when n=1, X and Z may represent a single bond, A represents an amino radical selected from the radicals having the formula:

in which $R_3$ and $R_4$ represent independently a hydrogen atom or an alkyl radical having 1–7 carbon atoms, or $R_3$ and $R_4$, together with the nitrogen atom to which they are attached, form a piperidino radical optionally substituted with a phenyl group or with a phenyl group and a cyano group, or a tetrahydropyridyl radical optionally substituted with a phenyl group, the radicals having the formula

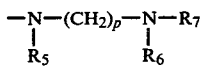

in which p is 2, 3 or 4, $R_5$ and $R_6$ are alkyl radicals having 1–7 carbon atoms and $R_7$ represents a phenoxy ($C_1$–$C_7$ alkyl) radical or a phenylthio ($C_1$–$C_7$ alkyl) radical, and the radicals having the formula

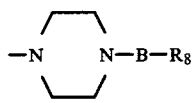

in which B represents a single bond, an alkylene radical having 1–10 carbon atoms or a hydroxyalkylene radical having 2–3 carbon atoms, and $R_8$ represents a hydrogen atom, a phenyl radical, a ($C_1$–$C_7$ alkyl) phenyl radical, a ($C_1$–$C_7$ alkoxy) phenyl radical, a phenoxy radical optionally mono-, di- or tri-substituted with an alkyl radical having 1–7 carbon atoms or an alkoxy radical having 1–7 carbon atoms, or a phenylthio, pyridyl or chromenyl radical, and their pharmaceutically acceptable acid addition salts.

Among said class, a particularly preferred class of compounds is that of the compounds of the formula (I) in which Z is a hydroxy radical or X and Z taken together form a single bond, and particularly those compounds in which A is a radical having the formula

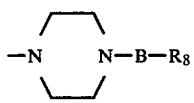

and most particularly

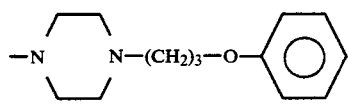

or a radical

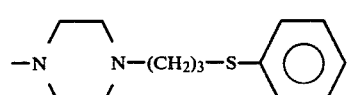

The compounds of the formula (I) may be prepared from compounds having the formula:

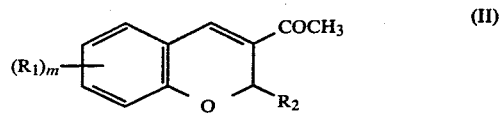

in which $R_1$, m and $R_2$ have the above-defined meanings.

Thus, the compounds of the formula (I) in which Y and Z represent together an oxygen atom and n=1 may be obtained by reaction of a compound of the formula (II) with an amine of the formula HA, in the presence of a formaldehyde source such as formaldehyde or trioxymethylene.

The Mannich reaction is generally effected in the following manner: one mole acetyl chromene of the formula (II) and 0.8 mole of amine HA as the hydrochloride are refluxed in one liter of solvent, ethanol, for example. It is frequently advantageous to add 1–2 ml concentrated hydrochloric acid. Trioxymethylene (3–6 moles) is generally added portionwise, over a period of time of 2–4 hours. The reaction is maintained under refluxing conditions for a period of time of 6 to 20 hours. A precipitate forms on cooling; this is suction filtered and crystallized. In some cases, it is necessary to remove a small amount of solvent to obtain said precipitate, or to add diethyl ether.

The compounds of the formula (I) in which Y and Z represent together an oxygen atom and in which n=0 may be obtained by bromination of a compound of the formula (II) and reaction of the resulting bromo compound of the formula

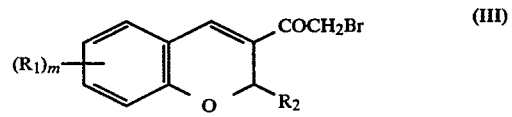

with an amine of the formula HA.

The bromo derivative (III) may be prepared by reacting at about 0° C. one mole bromine with one mole compound of the formula (II) dissolved in a solvent, generally diethyl ether, or else by reaction of cupric bromide with a compound of the formula (II) under refluxing conditions within an inert solvent.

The reaction of said bromo derivative with the amine is generally advantageously effected by reacting same mole for mole in the presence of two moles of an alkaline agent such as potassium carbonate within a solvent such as acetone, methylethylketone, for example. The reaction is effected in the cold, with stirring.

The ketonic compounds of the formula (I) thus prepared may be reduced to alcohols of the formula (I)-(Y=H and Z=OH) according to conventional methods, for example with $BH_4K$ in methanol.

The alcohols of the formula (I) may be etherified or esterified according to conventional methods, to give compounds of the formula (I) in which Y=H and Z=alkoxy or alkanoyloxy.

The compounds of the formula (I) in which X and Z represent a single bond, that is, the compounds of the formula:

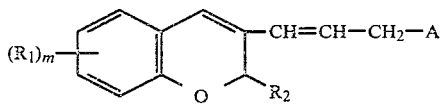 (IV)

may be obtained by dehydration, generally in acidic medium, of the compounds of the formula (I) in which Z is a hydroxy radical.

The following non limiting Examples illustrate the preparation of compounds of the formula (I).

EXAMPLE 1

1-(2H-3-chromenyl)-3-(N-methyl-piperazino)-1-propanone hydrochloride $R_1 = R_2 = H$; Y and $Z = O$; $n = 1$;

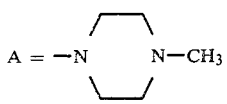
$A = -N\quad N-CH_3$

3-Acetyl-2H-chromene (0.5 mole) is dissolved in 250 ml ethanol, while warming. N-methyl-piperazine hydrochloride (0.4 mole) in ethanol (250 ml) and concentrated hydrochloric acid (1 ml) are added thereto. Trioxymethylene (3 moles) is added portionwise over 2 hours, and the resulting material is refluxed overnight. A pale yellow precipitate forms gradually. After cooling, the precipitate is filtered off, washed with ethanol and then with ether, after which it is dried in a desiccator at 90° C. and recrystallized from the minimum amount of water. M.p. = 228° C.

EXAMPLE 2

1-(2H-3-chromenyl)-3-(N-methylpiperazino)-1-propanol hydrochloride

The hydrochloride (0.1 mole) obtained in Example 1 is dissolved in methanol (400 ml). Sodium methoxide (0.22 mole) in methanol solution is added thereto. The material is cooled to 0°–5° C. and potassium borohydride (0.4 mole) is added thereto. The material is stirred overnight. It is then evaporated in vacuo without heating, taken up into ether/H₂O. The ethereal phase is washed with water, dried and evaporated, to give a pale yellow oil which is converted to the hydrochloride by addition of ethereal hydrochloric acid. M.p. = 220° C.

EXAMPLE 3

1-(2H-3-chromenyl)-2-(N-phenylpiperazino)-1-ethanone hydrochloride $R_1 = R_2 = H$; $n = 0$; Y and $Z = O$;

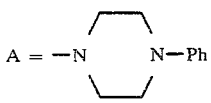
$A = -N\quad N-Ph$ (a) Preparation of 2-bromo-1-(2H-3-chromenyl)-1-ethanone 3-Acetyl-2H-chromene (0.2 mole) is dissolved in diethyl ether (250 ml) and methanol (10 ml). The solution is cooled to 0°–5° C. Bromine (0.21 mole) is added dropwise thereto, with stirring. The resulting material is left aside 2 hours at room temperature. Anhydrous potassium carbonate (25 g) is then added and the material is evaporated to dryness. The pasty residue is placed in a flask with 600 ml hexane, and is refluxed for 1 hour. The reaction mixture is decanted hot, allowed to cool, and the organic solution is placed in the freezer. Brown-yellow crystals having a sufficient purity for the next step separate out. After two recrystallizations from hexane, a sample gives long pale yellow needles, M.p. = 87° C.

| N.M.R. | δ: CH₂—Br | s 4 ppm 2H |
|---|---|---|
| | δ: CH₂—O | s 4.8 ppm 2H |

(b) 1-(2H-3-chromenyl)-2-(N-phenylpiperazino)-1-ethanone hydrochloride

N-phenylpiperazine (0.02 mole) is dissolved in anhydrous acetone (100 ml). Dry potassium carbonate (0.04 mole) is added thereto and the solution is cooled to 0°–5° C. A solution of the bromo derivative (0.02 mole) obtained in (a) in acetone (60 ml) is then slowly added. The mixture is allowed to revert to room temperature and is stirred overnight. The resulting material is poured over water, after which the resulting precipitate is filtered off and dried. It is then dissolved in isopropanol and converted to the hydrochloride by addition of ethereal hydrochloric acid. M.p. = 260° C. A sample of the base is recrystallized from isopropyl ether—M.p. = 165° C.

| N.M.R. (CCl₄) characteristic δ | |
|---|---|
| δ: —CH₂—O | s 5 ppm 2H |
| δ: —CO—CH₂— | s 3.5 ppm 2H |

EXAMPLE 4

1-(2H-3-Chromenyl)-2-(N-phenylpiperazino)-1-ethanol hydrochloride $R_1 = R_2 = H$; $n = 0$; $Y = H$; $Z = OH$;

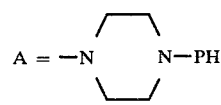
$A = -N\quad N-Ph$

The hydrochloride (0.01 mole) obtained in Example 3 is dissolved in methanol (200 ml). 40 ml of an 0.5 N solution of sodium methoxide in methanol is then added. The material is cooled to 0°–5° C. Potassium borohydride (0.03 mole) is then added portionwise. The material is allowed to revert to room temperature and is then stirred overnight, after which it is evaporated in vacuo at low temperature, taken up into ether and washed with water. The ether phase is dried and evaporated in vacuo. The resulting oil is recrystallized from methanol, to give white crystals, M.p. = 175° C.

| N.M.R. (CDCl₃) characteristic υ | |
|---|---|
| : —O—CH₂— (chromene) | s 4.8 ppm 2H |
| : H—C—OH | t 4 ppm 1H |
| : OH | s 3.9 ppm exchangeable D₂O 1H |

The characteristics of dihydrochlorides or monohydrochlorides of the compounds of Examples 1–4 are tabulated in the following Table, together with those of other hydrochlorides of compounds of the formula (I) (in which R₂=H) prepared in an analogous manner.
| Ex. | R₁ | n | Y | Z | A | M.P. |
|---|---|---|---|---|---|---|
| 1 | H | 1 | | O | 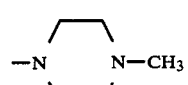 | 228° C. |
| 2 | H | 1 | H | OH | 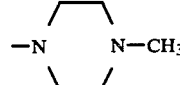 | 222° C. |
| 3 | H | 0 | | O | 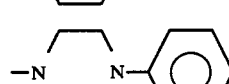 | 260° C. |
| 4 | H | 0 | H | OH | 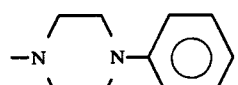 | 210° C. |
| 5 | H | 1 | | O | 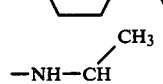 | 214° C. |
| 6 | H | 1 | H | OH | 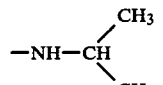 | 122° C. |
| 7 | H | 1 | | O | 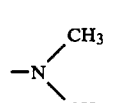 | 175° C. |
| 8 | H | 1 | H | OH | 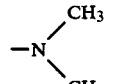 | 156° C. |
| 9 | H | 1 | | O | 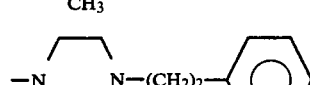 | 236° C. |
| 10 | H | 1 | H | OH | 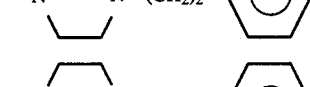 | 204° C. |
| 11 | H | 1 | | O | 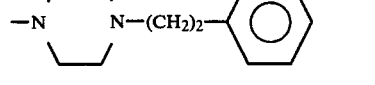 | 225° C. |
| 12 | H | 1 | H | OH | 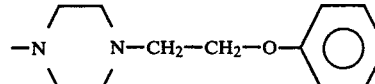 | 208° C. |
| 13 | H | 1 | | O | 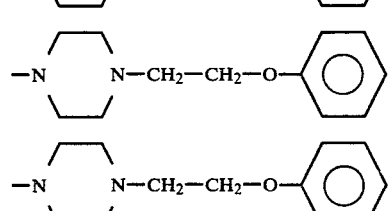 | 232° C. |
| 14 | H | 1 | H | OH | 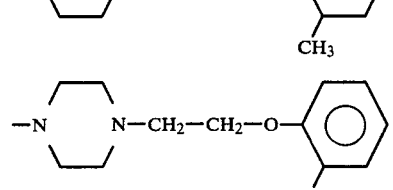 | 220° C. |

-continued
| Ex. | R₁ | n | Y | Z | A | M.P. |
|---|---|---|---|---|---|---|
| 15 | H | 1 | O | |  | 216° C. |
| 16 | H | 1 | H | OH | 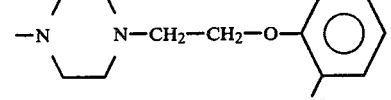 | 222° C. |
| 17 | H | 1 | O | |  | 230° C. |
| 18 | H | 1 | H | OH | 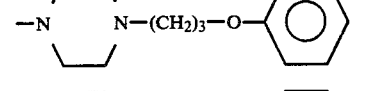 | 232° C. |
| 19 | H | 0 | O | | 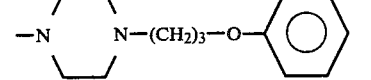 | 258° C. |
| 20 | H | 0 | H | OH | 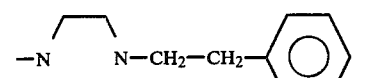 | 255° C. |
| 21 | H | 0 | O | |  | 225° C. |
| 22 | H | 0 | H | OH | 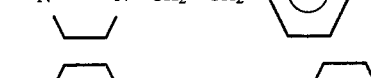 | 232° C. |
| 23 | H | 0 | O | | 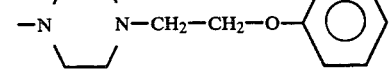 | 248° C. |
| 24 | H | 0 | H | OH | 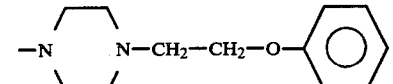 | 218° C. |
| 25 | H | 0 | O | |  | 218° C. |
| 26 | H | 0 | H | OH | 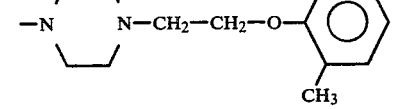 | 248° C. |
| 27 | H | 0 | H | OH |  | 186° C. |

| Ex. | R₁ | n | Y | Z | A | M.P. |
|---|---|---|---|---|---|---|
| 28 | H | 0 | H | OH | 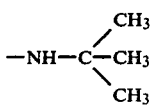 | 198° C. |
| 29 | H | 1 | O |  | 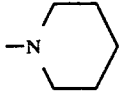 | 218° C. |
| 30 | H | 1 | H | OH | 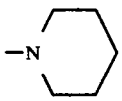 | 146° C. |
| 31 | H | 0 | O |  | 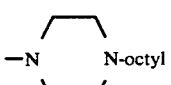 | 252° C. |
| 32 | H | 0 | H | OH | 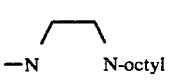 | 240° C. |
| 33 | H | 0 | O |  | 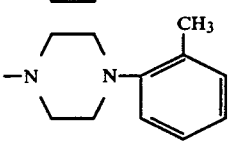 | 231° C. |
| 34 | H | 0 | H | OH | 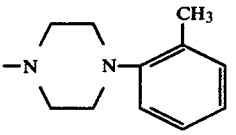 | 212° C. |
| 35 | H | 0 | O |  | 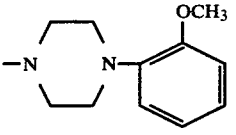 | 232° C. |
| 36 | H | 0 | H | OH | 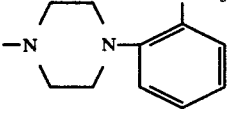 | 204° C. |
| 37 | H | 0 | O |  | 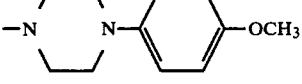 | 245° C. |
| 38 | H | 0 | H | OH | 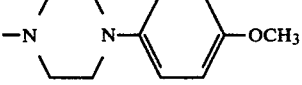 | 204° C. |
| 39 | H | 0 | O |  | 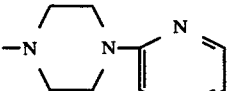 | 220° C. |
| 40 | H | 0 | H | OH | 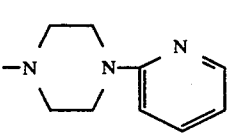 | 204° C. |
| 41 | H | 1 | O |  | 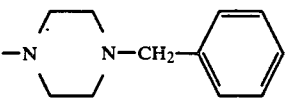 | 242° C. |

-continued

| Ex. | R₁ | n | Y | Z | A | M.P. |
|---|---|---|---|---|---|---|
| 42 | H | 1 | H | OH | −N(piperazine)N−CH₂−phenyl | 220° C. |
| 43 | H | 0 | | O | −N(piperazine)N−CH₂−phenyl | 225° C. |
| 44 | H | 0 | H | OH | −N(piperazine)N−CH₂−phenyl | 220° C. |
| 45 | H | 1 | | O | −N(piperazine)N−(CH₂)₃−phenyl | 240° C. |
| 46 | H | 1 | H | OH | −N(piperazine)N−(CH₂)₃−phenyl | 215° C. |
| 47 | H | 0 | | O | −N(piperazine)N−(CH₂)₃−phenyl | 278° C. |
| 48 | H | 0 | H | OH | −N(piperazine)N−(CH₂)₃−phenyl | 270° C. |
| 49 | H | 1 | | O | −N(piperazine)N−(CH₂)₃−O−(2,6-dimethylphenyl) | 246° C. |
| 50 | H | 1 | H | OH | −N(piperazine)N−(CH₂)₃−O−(2,6-dimethylphenyl) | 218° C. |
| 51 | H | 0 | | O | −N(piperazine)N−(CH₂)₃−O−(2,6-dimethylphenyl) | 220° C. |
| 52 | H | 0 | H | OH | −N(piperazine)N−(CH₂)₃−O−(2,6-dimethylphenyl) | 206° C. |
| 53 | H | 0 | | O | −N(piperazine)N−(CH₂)₃−O−(2,3,4-trimethoxyphenyl) | 200° C. |

-continued

| Ex. | R₁ | n | Y | Z | A | M.P. |
|---|---|---|---|---|---|---|
| 54 | H | 0 | H | OH | −N(piperazine)N−(CH₂)₃−O−(2,3,4-trimethoxyphenyl) | 198° C. |
| 55 | H | 1 |   | O | −N(CH₃)−(CH₂)₂−N(CH₃)−(CH₂)₃−O−phenyl | 265° C. |
| 56 | H | 1 | H | OH | −N(CH₃)−(CH₂)₂−N(CH₃)−(CH₂)₃−O−phenyl | 240° C. |
| 57 | H | 0 |   | O | −N(CH₃)−(CH₂)₂−N(CH₃)−(CH₂)₃−O−phenyl | 276° C. |
| 58 | H | 0 | H | OH | −N(CH₃)−(CH₂)₂−N(CH₃)−(CH₂)₃−O−phenyl | 255° C. |
| 59 | H | 1 |   | O | −N(piperazine)N−CH₂−CH(OH)−CH₂−O−phenyl | 228° C. |
| 60 | H | 1 | H | OH | −N(piperazine)N−CH₂−CH(OH)−CH₂−O−phenyl | 192° C. |
| 61 | H | 1 |   | O | −N(piperazine)N−(CH₂)₃−S−phenyl | 244° C. |
| 62 | H | 1 | H | OH | −N(piperazine)N−(CH₂)₃−S−phenyl | 222° C. |
| 63 | H | 0 |   | O | −N(piperazine)N−(CH₂)₃−S−phenyl | 250° C. |
| 64 | H | 0 | H | OH | −N(piperazine)N−(CH₂)₃−S−phenyl | 225° C. |
| 65 | H | 1 |   | O | −N(piperazine)N−(CH₂)₄−O−phenyl | 245° C. |
| 66 | H | 1 | H | OH | −N(piperazine)N−(CH₂)₄−O−phenyl | 238° C. |
| 67 | H | 0 |   | O | −N(piperazine)N−(CH₂)₄−O−phenyl | 222° C. |
| 68 | H | 0 | H | OH | −N(piperazine)N−(CH₂)₄−O−phenyl | 210° C. |

-continued
| Ex. | R₁ | n | Y | Z | A | M.P. |
|---|---|---|---|---|---|---|
| 69 | H | 1 | | O | 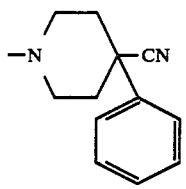 | 248° C. |
| 70 | H | 1 | H | OH | 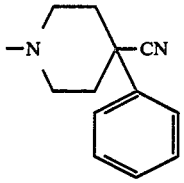 | 185° C. |
| 71 | H | 0 | | O | 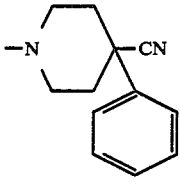 | 210° C. |
| 72 | H | 0 | H | OH | 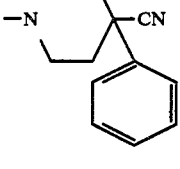 | 240° C. |
| 73 | H | 1 | | O | 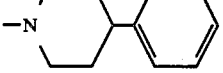 | 218° C. |
| 74 | H | 1 | H | OH | 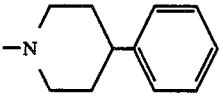 | 204° C. |
| 75 | H | 0 | | O | 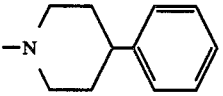 | 230° C. |
| 76 | H | 0 | H | OH | 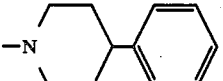 | 254° C. |
| 77 | H | 1 | | O | 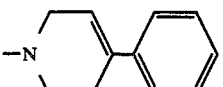 | 205° C. |
| 78 | H | 1 | H | OH | 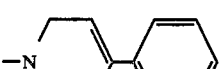 | 216° C. |
| 79 | H | 0 | | O | 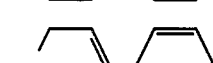 | 214° C. |
| 80 | H | 0 | H | OH | 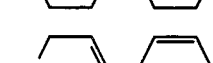 | 230° C. |

-continued

| Ex. | R₁ | n | Y | Z | A | M.P. |
|---|---|---|---|---|---|---|
| 81 | H | 0 | | O | 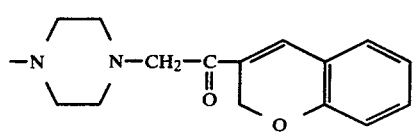 | 262° C. |
| 82 | H | 0 | H | OH | 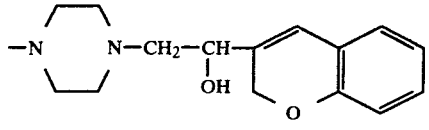 | 238° C. |
| 83 | 6-OMe | 1 | | O | 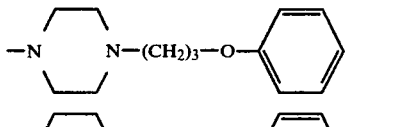 | 206° C. |
| 84 | 6-OMe | 1 | H | OH | 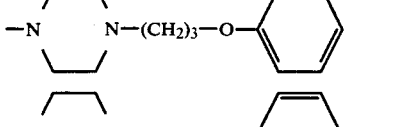 | 210° C. |
| 85 | 7-OMe | 1 | | O | 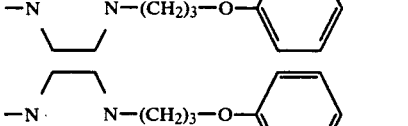 | 235° C. |
| 86 | 7-OMe | 1 | H | OH | 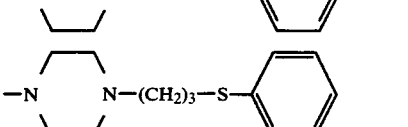 | 240° C. |
| 87 | 6-OMe | 1 | | O | 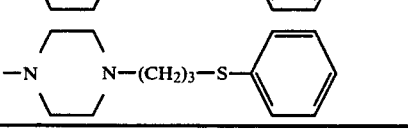 | 199° C. |
| 88 | 6-OMe | 1 | H | OH | 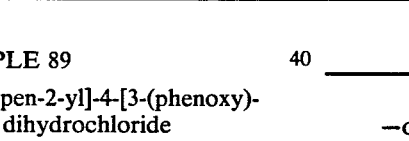 | 198° C. |

EXAMPLE 89

1-[(2H-3-chromenyl)-3-propen-2-yl]-4-[3-(phenoxy)-propyl]piperazine dihydrochloride (IV); R₁=R₂=H;

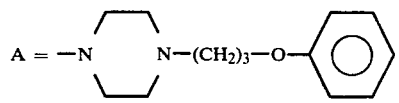

20 g of the hydrochloride of the aminoalcohol corresponding to Example 18 are dissolved in 50% ethanol-water. 6N Hydrochloric acid (20 ml) is added and the mixture is refluxed for 2 hours. Pearly scales precipitate on cooling; these are suction filtered and recrystallized from ethanol-water 60:40. M.p.=270°-275° C. (decomposition, 210° C.)

N.M.R. on the base (CDCl₃): 3 characteristics:

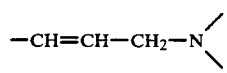  2H  3.3 ppm (d)

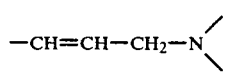  1H centered at about 5.8 ppm

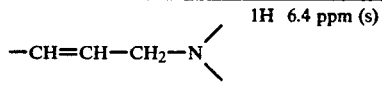  1H  6.4 ppm (s)

EXAMPLE 90

1-[(2H-3-chromenyl)-3-propen-2-yl]-4-[3-(phenylthio)-propyl]piperazine dihydrochloride (IV); R₁=R₂=H;

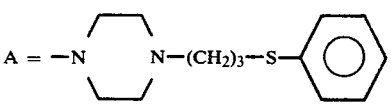

The material is prepared according to the procedure of Example 89. M.p.=275° C.

The compounds of the formula (I) and their pharmaceutically acceptable acid addition salts possess bronchodilator properties and a corrective activity of the anomalies of the cardiac rhythm, and are thus therapeutically useful as bronchodilator compounds for the treatment of asthma and as anti-arrhythmic compounds.

Results of pharmacological investigations which demonstrate said properties are given below.

(a) Bronchodilator activity

Preventive bronchodilator activity in guinea-pigs is investigated intravenously on the histamine induced bronchospasm according to the technique of H. Konzett and R. Rossler (Arch. Exp. Path. Pharmakol., 1949, 78, 210-224).

The compounds of the formula (I), administered at a single dosage of 0.5-3 mg/kg by the intravenous route induce a decrease of the bronchospasm by a factor of 25-85%. Said results are expressed as percent variation with respect to the amplitude of the reference bronchospams.

For example:

| Products | Dosages | % decrease of the bronchospasm |
|---|---|---|
| Example 4 | 1 mg | −83% |
| Example 10 | 1 mg | −71% |
| Example 12 | 1 mg | −60% |
| Example 18 | 1 mg | −70% |
| Example 42 | 0.5 mg | −26% |
| Example 60 | 1 mg | −55% |
| Example 62 | 0.5 mg | −81% |
| Example 66 | 0.5 mg | −30% |
| Example 70 | 0.5 mg | −72% |
| Example 84 | 0.5 mg | −81% |
| Example 86 | 0.5 mg | −49% |
| Example 89 | 1 mg | −63% |

(b) Corrective activity on the anomalies of the cardiac rhythm

Said activity was investigated in pentobarbital anesthetized dogs exhibiting arrhythmia and ventricular tachycardia after injection of a given dosage (40-100 γ/kg) of ouabaine. The compounds of the formula I, and more particularly the compounds 12, 14, 20, 26, 67 and 84, on intravenous administration at single dosages of 0.5-5 mg/kg produce a protection against ouabaine induced arrhythmia.

On the other hand, the compounds of the formula (I) were found to have little toxicity by the oral route and also by the intravenous route, both during investigation of the acute toxicity and of the chronic toxicity.

Thus, this invention includes also within its scope therapeutic compositions comprising, as active ingredient, a compound of the formula (I) or a pharmaceutically acceptable acid addition salt thereof, typically in combination with a pharmaceutically acceptable excipient.

The therapeutic compositions of this invention may be administered to humans by the oral or parenteral route or as inhalations. Said compositions may typically be formulated as capsules, tablets, injectable solutions or aerosols. The compositions may typically contain 1-80% active ingredient, depending on the route of administration. The daily dosage regimen in human patients may be from 20 mg to 1000 mg active ingredient.

Having now described our invention what We claim as new and desire to secure by Letters Patent is:

1. A compound selected from compounds of the general formula:

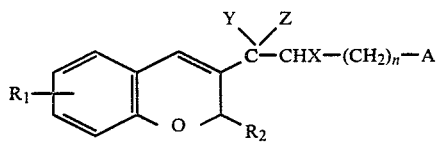

(I)

in which:
R$_1$ is selected from hydrogen and alkoxy having 1-7 carbon atoms,
R$_2$ is hydrogen,
n is selected from zero and 1,
X and Y are hydrogen atoms, and
Z is hydroxy, or
Y and Z taken together represent an oxygen atom, or, when n=1, X and Z may represent a single bond,
A represents an amino radical selected from the radicals of the formula:

in which R$_3$ and R$_4$ are independently selected from hydrogen and alkyl having 1-7 carbon atoms, or R$_3$ and R$_4$, together with the nitrogen atom to which they are attached, form a piperidino radical, a piperidino radical substituted with a phenyl group, a piperidino radical substituted with a phenyl group and a cyano group, or a tetrahydropyridyl radical, a tetrahydropyridyl radical substituted with a phenyl group, the radicals of the formula

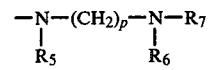

in which p is 2, 3 or 4, R$_5$ and R$_6$ are alkyl radicals having 1-7 carbon atoms and R$_7$ is selected from phenoxy (C$_1$-C$_7$ alkyl) and phenylthio (C$_1$-C$_7$ alkyl), and the radicals of the formula

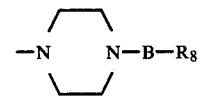

in which B is selected from a single bond, alkylene having 1-10 carbon atoms and hydroxyalkylene having 2-3 carbon atoms, and R$_8$ is selected from hydrogen, phenyl, (C$_1$-C$_7$ alkyl) phenyl, (C$_1$-C$_7$ alkoxy) phenyl, phenoxy, phenoxy mono-, di- or tri-substituted with alkyl having 1-7 carbon atoms, phenoxy mono-, di- or tri-substituted with alkoxy having 1-7 carbon atoms, phenylthio, pyridyl and chromenyl, and a pharmaceutically acceptable acid addition salt thereof.

2. Compounds as claimed in claim 1, wherein Z is a hydroxy radical or X and Z, taken together, form a single bond.

3. Compounds as claimed in claim 2, wherein A is a radical

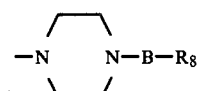

4. Compounds as claimed in claim 3, wherein A is a radical selected from the radical

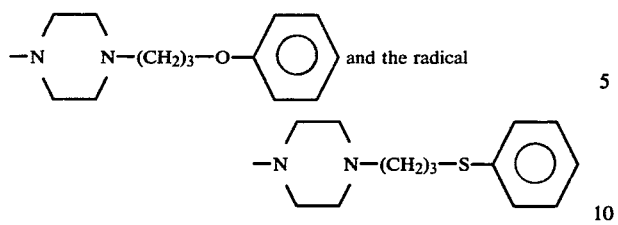 and the radical

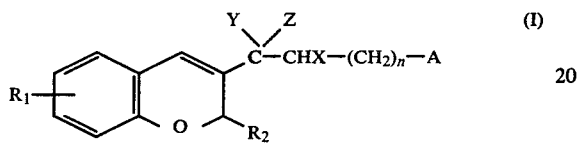

5. A pharmaceutical composition having a bronchodilator activity and an antiarrhythmic activity containing a bronchodilator and antiarrhythmic effective amount of a compound selected from compounds of the general formula:

$$\begin{array}{c} Y \diagdown Z \\ C-CHX-(CH_2)_n-A \end{array} \quad (I)$$

(with $R_1$ on benzene ring, $R_2$ on O-bearing carbon)

in which:
$R_1$ is selected from hydrogen and alkoxy having 1–7 carbon atoms,
$R_2$ is hydrogen,
n is selected from zero and 1,
X and Y are hydrogen atoms, and
Z is hydroxy, or
Y and Z taken together represent an oxygen atom, or, when n=1, X and Z may represent a single bond,
A represents an amino radical selected from the radicals of the formula:

in which $R_3$ and $R_4$ are independently selected from hydrogen and alkyl having 1–7 carbon atoms, or $R_3$ and $R_4$, together with the nitrogen atom to which they are attached, form a piperidino radical, a piperidino radical substituted with a phenyl group, a piperidino radical substituted with a phenyl group and a cyano group, or a tetrahydropyridyl radical, a tetrahydropyridyl radical substituted with a phenyl group,
the radicals of the formula

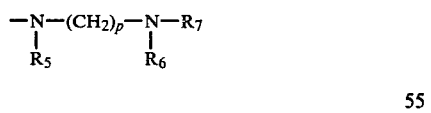

in which p is 2, 3 or 4, $R_5$ and $R_6$ are alkyl radicals having 1–7 carbon atoms and $R_7$ is selected from phenoxy ($C_1$–$C_7$ alkyl) and phenylthio ($C_1$–$C_7$ alkyl), and
the radicals of the formula

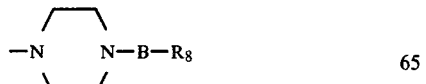

in which B is selected from a single bond, alkylene having 1–10 carbon atoms and hydroxyalkylene having 2–3 carbon atoms, and $R_8$ is selected from hydrogen, phenyl, ($C_1$–$C_7$ alkyl) phenyl, ($C_1$–$C_7$ alkoxy), phenyl, phenoxy, phenoxy mono-, di- or tri-substituted with alkyl having 1–7 carbon atoms, phenoxy mono-, di- or tri-substituted with alkoxy having 1–7 carbon atoms, phenylthio, pyridyl and chromenyl, and a pharmaceutically acceptable acid addition salt thereof, and a pharmaceutically acceptable excipient.

6. A process for the treatment of the anomalies of the cardiac rhythm comprising administering to a human in need thereof a pharmaceutical composition containing an antiarrhythmic effective amount of a compound selected from compounds of the general formula:

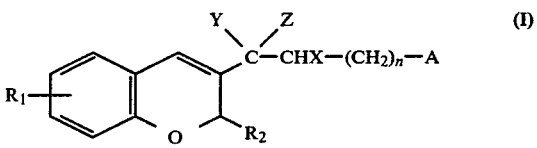

in which:
$R_1$ is selected from hydrogen and alkoxy having 1–7 carbon atoms,
$R_2$ is hydrogen,
n is selected from zero and 1,
X and Y are hydrogen atoms, and
Z is hydroxy, or
Y and Z taken together represent an oxygen atom, or, when n=1, X and Z may represent a single bond,
A represents an amino radical selected from the radicals of the formula:

in which $R_3$ and $R_4$ are independently selected from hydrogen and alkyl having 1–7 carbon atoms, or $R_3$ and $R_4$, together with the nitrogen atom to which they are attached, form a piperidino radical, a piperidino radical substituted with a phenyl group, a piperidino radical substituted with a phenyl group and a cyano group, or a tetrahydropyridyl radical, a tetrahydropyridyl radical substituted with a phenyl group, the radicals of the formula

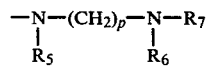

in which p is 2, 3 or 4, $R_5$ and $R_6$ are alkyl radicals having 1–7 carbon atoms and $R_7$ is selected from phenoxy ($C_1$–$C_7$ alkyl) and phenylthio ($C_1$–$C_7$ alkyl), and the radicals of the formula

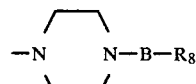

in which B is selected from a single bond, alkylene having 1-10 carbon atoms and hydroxyalkylene having 2-3 carbon atoms, and $R_8$ is selected from hydrogen, phenyl, ($C_1$-$C_7$ alkyl) phenyl, ($C_1$-$C_7$ alkoxy) phenyl, phenoxy, phenoxy mono-, di- or tri-substituted with alkyl having 1-7 carbon atoms, phenoxy mono-, di- or tri-substituted with alkoxy having 1-7 carbon atoms, phenylthio, pyridyl and chromenyl, and a pharmaceutically acceptable acid addition salt thereof.

7. A process as claimed in claim 6, comprising administering from 20 to 1000 mg of active ingredient per day.

8. Process for the treatment of asthma which comprises administering to a human in need thereof a pharmaceutical composition comprising a bronchodilator effective amount of a compound selected from compounds of the general formula:

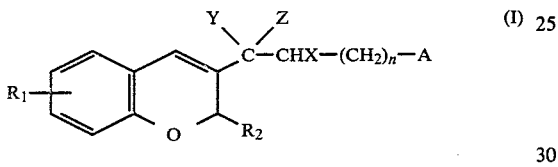

in which:

$R_1$ is selected from hydrogen and alkoxy having 1-7 carbon atoms, $R_2$ is hydrogen, n is selected from zero and 1, X and Y are hydrogen atoms, and Z is hydroxy, or Y and Z taken together represent an oxygen atom, or, when n=1, X and Z may represent a single bond, A represents an amino radical selected from the radicals of the formula:

in which $R_3$ and $R_4$ are independently selected from hydrogen and alkyl having 1-7 carbon atoms, or $R_3$ and $R_4$, together with the nitrogen atom to which they are attached, form a piperidino radical, a piperidino radical substituted with a phenyl group, a piperidino radical substituted with a phenyl group and a cyano group, or a tetrahydropyridyl radical, a tetrahydropyridyl radical substituted with a phenyl group, the radicals of the formula

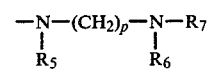

in which p is 2, 3 or 4, $R_5$ and $R_6$ are alkyl radicals having 1-7 carbon atoms and $R_7$ is selected from phenoxy ($C_1$-$C_7$ alkyl) and phenylthio ($C_1$-$C_7$ alkyl), and the radicals of the formula

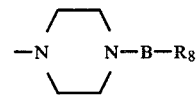

in which B is selected from a single bond, alkylene having 1-10 carbon atoms and hydroxyalkylene having 2-3 carbon atoms, and $R_8$ is selected from hydrogen, phenyl, ($C_1$-$C_7$ alkyl) phenyl, ($C_1$-$C_7$ alkoxy) phenyl, phenoxy, phenoxy mono-, di- or tri-substituted with alkyl having 1-7 carbon atoms, phenoxy mono-, di- or tri-substituted with alkoxy having 1-7 carbon atoms, phenylthio, pyridyl and chromenyl, and a pharmaceutically acceptable acid addition salt thereof.

* * * * *